US009731135B2

(12) United States Patent
Arcot-Krishnamurthy et al.

(10) Patent No.: US 9,731,135 B2
(45) Date of Patent: Aug. 15, 2017

(54) AUTOMATIC SELECTION OF LEAD CONFIGURATION FOR A NEURAL STIMULATION LEAD

(71) Applicant: Cardiac Pacemakers, Inc., St. Paul, MN (US)

(72) Inventors: Shantha Arcot-Krishnamurthy, Renton, WA (US); David J. Ternes, Roseville, MN (US); Jason J. Hamann, Blaine, MN (US); Juan Gabriel Hincapie Ordonez, Maple Grove, MN (US); Stephen B. Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/733,160

(22) Filed: Jun. 8, 2015

(65) Prior Publication Data
US 2015/0290462 A1 Oct. 15, 2015

Related U.S. Application Data

(63) Continuation of application No. 13/893,080, filed on May 13, 2013, now Pat. No. 9,050,472, which is a (Continued)

(51) Int. Cl.
*A61N 1/00* (2006.01)
*A61N 1/36* (2006.01)
*A61N 1/372* (2006.01)

(52) U.S. Cl.
CPC ..... *A61N 1/36139* (2013.01); *A61N 1/36053* (2013.01); *A61N 1/36128* (2013.01);
(Continued)

(58) Field of Classification Search
CPC ............ A61N 1/36053; A61N 1/36114; A61N 1/36185; A61N 1/371; A61N 1/3712; A61N 1/3605; A61N 1/37; A61N 1/3702
See application file for complete search history.

(56) References Cited

U.S. PATENT DOCUMENTS 4,177,818 A 12/1979 De Pedro
4,573,481 A 3/1986 Bullara
(Continued)

FOREIGN PATENT DOCUMENTS

EP 0585553 A1 6/1993
JP 2005058456 A 3/2005
(Continued)

OTHER PUBLICATIONS

International Preliminary Examination Report issued in PCT/US2013/000654 completed Apr. 16, 2015, 9 pages.
(Continued)

*Primary Examiner* — Scott Getzow
(74) *Attorney, Agent, or Firm* — Schwegman Lundberg & Woessner, P.A.

(57) ABSTRACT

A neurostimulation system includes a neural stimulation lead having a proximal portion and a distal portion and including a plurality of electrodes along the distal portion. The plurality of electrodes are configured for positioning proximate a portion of the autonomic nervous system. A neural stimulation circuit, coupled to the plurality of electrodes, delivers neural stimulation pulses to the plurality of electrodes. A processor and controller is configured to control the neural stimulation circuit to deliver first neural stimulation pulses to each of a plurality of electrode configurations. Each electrode configuration includes one or more of the plurality of electrodes. The processor and controller is further configured to receive information related to motor fiber activity that is induced in response to
(Continued)

delivery of the first neural stimulation pulses to each of the plurality of electrode configurations and to identify the electrode configurations that induce the motor fiber activity.

20 Claims, 6 Drawing Sheets

Related U.S. Application Data continuation of application No. 13/220,423, filed on Aug. 29, 2011, now Pat. No. 8,452,406.

(60) Provisional application No. 61/383,192, filed on Sep. 15, 2010.

(52) U.S. Cl.
CPC ..... *A61N 1/36146* (2013.01); *A61N 1/36185* (2013.01); *A61N 1/37235* (2013.01); *A61N 1/37288* (2013.01)

(56) References Cited

U.S. PATENT DOCUMENTS

| | | | |
|---|---|---|---|
| 4,590,946 A | 5/1986 | Loeb |
| 4,590,949 A | 5/1986 | Pohndorf |
| 4,602,624 A | 7/1986 | Naples et al. |
| 4,628,942 A | 12/1986 | Sweeney et al. |
| 4,740,170 A | 4/1988 | Lee et al. |
| 4,920,979 A | 5/1990 | Bullara |
| 4,940,065 A | 7/1990 | Tanagho et al. |
| 4,979,511 A | 12/1990 | Terry, Jr. |
| 5,031,621 A | 7/1991 | Grandjean et al. |
| 5,095,905 A | 3/1992 | Klepinski |
| 5,215,089 A | 6/1993 | Baker et al. |
| 5,218,089 A | 6/1993 | Mariotti et al. |
| 5,251,634 A | 10/1993 | Weinberg |
| 5,259,394 A | 11/1993 | Bens |
| 5,282,468 A | 2/1994 | Klepinski |
| 5,324,322 A | 6/1994 | Grill, Jr. et al. |
| 5,334,438 A | 8/1994 | Saugnac |
| 5,344,438 A | 9/1994 | Testerman et al. |
| 5,351,394 A | 10/1994 | Weinberg |
| 5,358,516 A | 10/1994 | Myers et al. |
| 5,375,594 A | 12/1994 | Cueva |
| 5,505,201 A | 4/1996 | Grill et al. |
| 5,531,778 A | 7/1996 | Maschino et al. |
| 5,674,272 A | 10/1997 | Bush et al. |
| 5,689,877 A | 11/1997 | Grill et al. |
| 5,755,766 A | 5/1998 | Chastain et al. |
| 5,782,892 A | 7/1998 | Castle et al. |
| 5,871,530 A | 2/1999 | Williams et al. |
| 5,913,876 A | 6/1999 | Taylor et al. |
| 5,964,702 A | 10/1999 | Grill et al. |
| 6,038,479 A | 3/2000 | Werner et al. |
| 6,051,017 A | 4/2000 | Loeb et al. |
| 6,093,197 A | 7/2000 | Bakula et al. |
| 6,174,329 B1 | 1/2001 | Callol et al. |
| 6,178,349 B1 | 1/2001 | Kieval |
| 6,249,708 B1 | 6/2001 | Nelson et al. |
| 6,292,703 B1 | 9/2001 | Meier et al. |
| 6,296,659 B1 | 10/2001 | Foerster |
| 6,308,104 B1 | 10/2001 | Taylor et al. |
| 6,308,105 B1 | 10/2001 | Duysens et al. |
| 6,381,499 B1 | 4/2002 | Taylor et al. |
| 6,423,080 B1 | 7/2002 | Gellman et al. |
| 6,600,956 B2 | 7/2003 | Maschino et al. |
| 6,725,096 B2 | 4/2004 | Chinn et al. |
| 7,047,081 B2 | 5/2006 | Kuzma |
| 7,054,692 B1 | 5/2006 | Whitehurst et al. |
| 7,160,298 B2 | 1/2007 | Lawew et al. |
| 7,212,867 B2 | 5/2007 | Van Venrooij et al. |
| 7,502,650 B2 | 3/2009 | Kieval |
| 7,536,227 B1 | 5/2009 | Poore et al. |
| 7,561,923 B2 | 7/2009 | Libbus et al. |
| 7,711,421 B2 | 5/2010 | Shafer et al. |
| 7,749,273 B2 | 7/2010 | Cauthen, III et al. |
| 7,807,925 B2 | 10/2010 | Zarembo |
| 7,831,311 B2 | 11/2010 | Cross, Jr. et al. |
| 7,891,085 B1 | 2/2011 | Kuzma et al. |
| 7,925,352 B2 | 4/2011 | Stack et al. |
| 7,925,358 B2 | 4/2011 | Belden et al. |
| 7,933,662 B2 | 4/2011 | Marshall et al. |
| 7,957,817 B1 | 6/2011 | Gillespie et al. |
| 7,974,706 B2 | 7/2011 | Moffitt et al. |
| 7,996,092 B2 | 8/2011 | Mrva et al. |
| 8,100,141 B2 | 1/2012 | Slupecki et al. |
| 8,155,757 B1 | 4/2012 | Neisz et al. |
| 8,244,372 B1 | 8/2012 | Zhulati et al. |
| 8,295,948 B2 | 10/2012 | Barker et al. |
| 8,326,418 B2 | 12/2012 | Sommer et al. |
| 8,417,343 B2 | 4/2013 | Bolea et al. |
| 8,452,406 B2 | 5/2013 | Arcot-Krishnamurthy et al. |
| 8,483,845 B2 | 7/2013 | Sage |
| 8,548,593 B2 | 10/2013 | Ternes et al. |
| 8,639,355 B2 | 1/2014 | Soltis |
| 9,037,239 B2* | 5/2015 | Brooke .............. A61N 1/36185 607/27 |
| 9,050,472 B2 | 6/2015 | Arcot-Krishnamurthy et al. |
| 2002/0116042 A1 | 8/2002 | Boling |
| 2002/0128700 A1 | 9/2002 | Cross, Jr. |
| 2003/0040785 A1 | 2/2003 | Maschino et al. |
| 2003/0236558 A1 | 12/2003 | Whitehurst et al. |
| 2004/0010303 A1 | 1/2004 | Bolea et al. |
| 2004/0111139 A1 | 6/2004 | McCreery |
| 2005/0209655 A1 | 9/2005 | Bradley et al. |
| 2005/0234512 A1 | 10/2005 | Nakao |
| 2005/0283246 A1 | 12/2005 | Cauthen, III et al. |
| 2006/0030919 A1 | 2/2006 | Mrva et al. |
| 2006/0122675 A1 | 6/2006 | Libbus et al. |
| 2006/0190042 A1 | 8/2006 | Stone et al. |
| 2006/0259078 A1 | 11/2006 | Libbus |
| 2007/0071568 A1 | 3/2007 | Dorstewitz |
| 2007/0083236 A1 | 4/2007 | Sikora et al. |
| 2007/0100406 A1 | 5/2007 | Kollatschny et al. |
| 2007/0118177 A1 | 5/2007 | Libbus et al. |
| 2007/0142871 A1 | 6/2007 | Libbus et al. |
| 2007/0173914 A1 | 7/2007 | Kollatschny |
| 2007/0203556 A1 | 8/2007 | Rutten et al. |
| 2007/0239243 A1 | 10/2007 | Moffitt et al. |
| 2007/0255320 A1 | 11/2007 | Inman et al. |
| 2008/0046058 A1 | 2/2008 | Cross et al. |
| 2008/0051839 A1 | 2/2008 | Libbus et al. |
| 2008/0058871 A1 | 3/2008 | Libbus et al. |
| 2008/0058874 A1 | 3/2008 | Westlund et al. |
| 2008/0058901 A1 | 3/2008 | Ternes et al. |
| 2008/0086181 A1 | 4/2008 | Amurthur et al. |
| 2008/0091255 A1 | 4/2008 | Caparso et al. |
| 2008/0103407 A1 | 5/2008 | Bolea et al. |
| 2008/0103545 A1 | 5/2008 | Bolea et al. |
| 2008/0132987 A1 | 6/2008 | Westlund et al. |
| 2008/0140092 A1 | 6/2008 | Stone et al. |
| 2008/0172101 A1 | 7/2008 | Bolea et al. |
| 2008/0177365 A1 | 7/2008 | Bolea et al. |
| 2008/0177366 A1 | 7/2008 | Bolea et al. |
| 2008/0183258 A1 | 7/2008 | Inman |
| 2008/0195188 A1 | 8/2008 | Libbus et al. |
| 2008/0234780 A1 | 9/2008 | Smith et al. |
| 2008/0255613 A1 | 10/2008 | Kaiser et al. |
| 2009/0043351 A1* | 2/2009 | Sathaye .............. A61N 1/3686 607/28 |
| 2009/0048641 A1 | 2/2009 | Libbus |
| 2009/0210042 A1 | 8/2009 | Kowalczewski |
| 2009/0259260 A1 | 10/2009 | Bentley et al. |
| 2009/0275997 A1 | 11/2009 | Faltys et al. |
| 2009/0276024 A1 | 11/2009 | Bonde et al. |
| 2009/0318961 A1 | 12/2009 | Stone et al. |
| 2010/0023088 A1 | 1/2010 | Stack et al. |
| 2010/0036451 A1 | 2/2010 | Hoffer |
| 2010/0121405 A1 | 5/2010 | Ternes et al. |
| 2010/0145221 A1 | 6/2010 | Brunnett et al. |
| 2010/0168831 A1 | 7/2010 | Korivi et al. |

(56) References Cited

U.S. PATENT DOCUMENTS

| | | | |
|---|---|---|---|
| 2010/0211131 A1 | 8/2010 | Williams et al. | |
| 2010/0286553 A1 | 11/2010 | Feler et al. | |
| 2010/0305674 A1 | 12/2010 | Zarembo et al. | |
| 2010/0312320 A1 | 12/2010 | Faltys et al. | |
| 2010/0331938 A1 | 12/2010 | Sommer et al. | |
| 2011/0004264 A1* | 1/2011 | Siejko | A61N 1/371 607/28 |
| 2011/0004281 A1 | 1/2011 | Jones | |
| 2011/0022142 A1 | 1/2011 | Barker et al. | |
| 2011/0040257 A1 | 2/2011 | Behymer et al. | |
| 2011/0060395 A1 | 3/2011 | Cantlon | |
| 2011/0172682 A1 | 7/2011 | Brady et al. | |
| 2011/0172701 A1 | 7/2011 | Wales et al. | |
| 2012/0022617 A1 | 1/2012 | Tockman et al. | |
| 2012/0035691 A1 | 2/2012 | Tockman et al. | |
| 2012/0065702 A1 | 3/2012 | Arcot-Krishnamurthy et al. | |
| 2012/0158082 A1 | 6/2012 | Katra | |
| 2012/0221087 A1 | 8/2012 | Parnis et al. | |
| 2013/0005169 A1 | 1/2013 | Soltis et al. | |
| 2013/0013045 A1 | 1/2013 | Soltis | |
| 2013/0172973 A1 | 7/2013 | Tockman et al. | |
| 2013/0253615 A1 | 9/2013 | Arcot-Krishnamurthy et al. | |
| 2013/0253624 A1 | 9/2013 | Tockman et al. | |
| 2014/0094888 A1 | 4/2014 | True et al. | |

FOREIGN PATENT DOCUMENTS

| | | |
|---|---|---|
| JP | 2008526299 A | 7/2008 |
| WO | WO9929366 A1 | 6/1999 |
| WO | WO2004052176 A2 | 6/2004 |
| WO | WO2006093685 A1 | 9/2006 |
| WO | WO2007024164 A1 | 1/2007 |
| WO | WO2008088798 A1 | 7/2008 |
| WO | WO-2008088798 A1 | 7/2008 |
| WO | WO2008094349 A1 | 8/2008 |
| WO | WO2009020639 A1 | 2/2009 |
| WO | WO2009025817 A2 | 2/2009 |
| WO | WO2009100242 A2 | 8/2009 |
| WO | WO2011053766 A1 | 5/2011 |
| WO | WO-2012036883 A1 | 3/2012 |
| WO | 2013142053 A1 | 9/2013 |

OTHER PUBLICATIONS

International Preliminary Examination Report, Chapter II, issued in PCT/US2013/029306, completed Aug. 19, 2014, 16 pages.
International Preliminary Report on Patentability issued in PCT/US2013/062608, completed Apr. 7, 2015, 8 pages.
International Search Report and Written Opinion Issued in PCT/US2009/063442, mailed Feb. 1, 2010, 11 pages.
International Search Report and Written Opinion issued in PCT/US2010/026350, mailed Jun. 2, 2010.
International Search Report and Written Opinion issued in PCT/US2011/020699, mailed Jul. 26, 2011, 24 pages.
International Search Report and Written Opinion Issued in PCT/US2011/049585, mailed Dec. 19, 2011.
International Search Report and Written Opinion Issued in PCT/US2012/044020, mailed Sep. 11, 2012, 9 pages.
International Search Report and Written Opinion issued in PCT/US2012/044028, mailed Oct. 1, 2012, 9 pages.
International Search Report and Written Opinion issued in PCT/US2012/071812, mailed Sep. 13, 2013, 12 pages.
International Search Report and Written Opinion issued in PCT/US2013/029306, mailed Jul. 18, 2013, 13 pages.
International Search Report and Written Opinion issued in PCT/US2013/062560, mailed Dec. 17, 2014, 13 pages.
International Search Report and Written Opinion issued in PCT/US2013/062608, mailed Dec. 17, 2014, 13 pages.
International Search Report and Written Opinion issued in PCT/US2013/077949, mailed Jun. 20, 2014, 15 pages.
International Search Report and Written Opinion issued in PCT/US2014/015590, mailed May 28, 2014, 14 pages.
Kirsch, Robert F. et al., "Restoration of Hand and Arm Function by Functional Neuromuscular Stimulation", Period covered: Jun. 1, 2001-Aug. 31, 2006, 71 pages.
Partial International Search Report issued in PCT/US2011/020699, mailed Mar. 24, 2011, 6 pages.
Written Opinion of the International Preliminary Examining Authority issued in PCT/US2013/029306, mailed May 8, 2014, 6 pages.
"European Application Serial No. 11754800.8, Office Action mailed Apr. 23, 2013", 2 pgs.
"European Application Serial No. 11754800.8, Response filed Oct. 24, 2013 to Office Action mailed Apr. 23, 2013", 14 pgs.
"European Application Serial No. 15193293.6, Extended European Search Report mailed Mar. 9, 2016", 7 pgs.

* cited by examiner

AUTOMATIC SELECTION OF LEAD CONFIGURATION FOR A NEURAL STIMULATION LEAD

CROSS-REFERENCE TO RELATED APPLICATION

This application is a continuation of U.S. patent application Ser. No. 13/893,080, filed May 13, 2013, now issued as U.S. Pat. No. 9,050,472, which is a continuation of U.S. patent application Ser. No. 13/220,423, filed Aug. 29, 2011, now issued as U.S. Pat. No. 8,452,406, which claims priority to Provisional Application No. 61/383,192, filed Sep. 15, 2010, each of which are herein incorporated by reference in their entirety.

TECHNICAL FIELD

The present invention relates generally to implantable medical devices. More specifically, the present invention relates to automatic selection of lead electrode configurations for medical device leads.

BACKGROUND

A significant amount of research has been directed both to the direct and indirect stimulation and sensing of the left and right vagus nerves, the phrenic nerve, the sacral nerve, the cavernous nerve, and portions of the anatomy with baroreceptors (e.g., the carotid artery) to treat a wide variety of medical, psychiatric, and neurological disorders or conditions. For example, stimulation of the vagus nerve has been proposed as a method for treating various heart conditions, including heart failure. The nerves stimulated and/or sensed may be sympathetic or parasympathetic in character.

In a nerve stimulation and sensing system, one or more electrodes are formed on a lead that are electrically connected to an implanted electronic package, such as a pulse generator. Electrical energy is delivered to the electrodes by conductors that extend from the pulse generator at a proximal end of the lead to the electrodes at a distal end of the lead. For direct stimulation of a nerve, the electrodes may be configured to be secured directly to, wrapped around, or positioned next to the nerve.

SUMMARY

Discussed herein are systems and methods for automatically selecting electrode configurations for a neural stimulation lead by prioritizing the electrode configurations with the most neural capture based on the degree of physiological activity and therapeutic effect induced by neural stimulation signals.

In Example 1, a neurostimulation system includes a neural stimulation lead, a neural stimulation circuit, and a processor and controller. The neural stimulation lead has a proximal portion and a distal portion and includes a plurality of electrodes along the distal portion. The plurality of electrodes are configured for positioning proximate a portion of the autonomic nervous system. The neural stimulation circuit, coupled to the plurality of electrodes, delivers neural stimulation pulses to the plurality of electrodes. The processor and controller is configured to control the neural stimulation circuit to deliver first neural stimulation pulses to each of a plurality of electrode configurations. Each electrode configuration includes one or more of the plurality of electrodes. The processor and controller is further configured to receive information related to motor fiber activity that is induced in response to delivery of the first neural stimulation pulses to each of the plurality of electrode configurations and to identify the electrode configurations that induce the motor fiber activity.

In Example 2, the neurostimulation system according to Example 1, wherein the processor and controller is configured to control the neural stimulation circuit to deliver the first neural stimulation pulses at more than one energy level to each of the plurality of electrode configurations.

In Example 3, the neurostimulation system according to either Example 1 or 2, wherein the processor and controller is further configured to prioritize the plurality of electrode configurations based on a first capture threshold for the motor fiber activity.

In Example 4, the neurostimulation system according to Example 3, wherein the processor and controller further controls the neural stimulation circuit to deliver second neural stimulation pulses to one or more electrode configurations with a lowest first capture threshold for motor fiber activity and to receive information related to one or more physiological responses that are induced in response to delivery of the second neural stimulation pulses to each of the plurality of electrode configurations.

In Example 5, the neurostimulation system according to any of Examples 1-4, and further comprising one or more physiological activity sensors configured to sense a signal indicative of the one or more physiological responses and generate the information related to the one or more physiological responses.

In Example 6, the neurostimulation system according to Example 4, wherein the one or more physiological responses include intended physiological activity and intolerable physiological activity, and wherein the processor and controller is further configured to eliminate the electrode configurations that induce intolerable physiological activity and to prioritize the one or more electrode configurations that induce intended physiological activity based on a second capture threshold for the intended physiological activity.

In Example 7, the neurostimulation system according to any of Examples 1-6, wherein the processor and controller is programmable to deliver therapy to at least one of the one or more electrode configurations that induce intended physiological activity at a lowest second capture threshold.

In Example 8, the neurostimulation system according to any of Examples 1-7, and further comprising an activity sensor configured to sense a signal indicative of motor fiber activity and generate the information related to the motor fiber activity.

In Example 9, a method includes coupling a plurality of electrodes to a neural stimulation circuit that delivers neural stimulation pulses to the plurality of electrodes, the plurality of electrodes positioned proximate a portion of the autonomic nervous system. The method also includes controlling the neural stimulation circuit to deliver first neural stimulation pulses to each of a plurality of electrode configurations. Each electrode configuration comprises one or more of the plurality of electrodes. The method further includes receiving information related to motor fiber activity that is induced in response to delivery of the first neural stimulation pulses to each of the plurality of electrode configurations and identifying the electrode configurations that induce the motor fiber activity.

In Example 10, the method according to Example 9, wherein the controlling step comprises controlling the neural stimulation circuit to deliver the first neural stimulation pulses at more than one energy level to each of the plurality of electrode configurations.

In Example 11, the method according to either Example 9 or 10, further comprising prioritizing the plurality of electrode configurations based on a first capture threshold for the motor fiber activity.

In Example 12, the method according to Example 11, and further comprising controlling the neural stimulation circuit to deliver second neural stimulation pulses to one or more electrode configurations with a lowest first capture threshold for motor fiber activity; and receiving information related to one or more physiological responses that are induced in response to delivery of the second neural stimulation pulses to each of the plurality of electrode configurations.

In Example 13, the method according to Example 12, wherein the one or more physiological responses include intended physiological activity and intolerable physiological activity, and wherein the method further comprises eliminating the electrode configurations that induce intolerable physiological activity and prioritizing the one or more electrode configurations that induce intended physiological activity based on a second capture threshold for the intended physiological activity.

In Example 14, the method according to any of Examples 9-13, and further comprising delivering therapy to at least one of the one or more electrode configurations that induce intended physiological activity at a lowest second capture threshold.

In Example 15, a method includes positioning a plurality of electrodes proximate a portion of the autonomic nervous system, the plurality of electrodes disposed along a distal portion of a neural stimulation lead. The neural stimulation lead is coupled to an external device configured to deliver first neural stimulation pulses to the plurality of electrodes. The external device is then controlled to deliver first neural stimulation pulses at more than one energy level to each of a plurality of electrode configurations. Each electrode configuration includes one or more of the plurality of electrodes. Information is provided to the external device related to motor fiber activity that is induced in response to delivery of the first neural stimulation pulses to each of the plurality of electrode configurations. An output is generated on the external device that prioritizes the plurality of electrode configurations based on a first capture threshold for the motor fiber activity.

In Example 16, the method according to Example 15, and further comprising coupling the neural stimulation lead to an implantable medical device (IMD).

In Example 17, the method according to Example 16, wherein, after the IMD has been implanted for a period of time, the method further comprises controlling the IMD to deliver the first neural stimulation pulses at more than one energy level to each of the plurality of electrode configurations. Information is provided from the IMD to the external device related to motor fiber activity that is induced in response to delivery of the first neural stimulation pulses by the IMD to each of the plurality of electrode configurations. An output is generated on the external device that prioritizes the plurality of electrode configurations based on the first capture threshold for the motor fiber activity.

In Example 18, the method according to Example 17, and further comprising programming the IMD with the external device to deliver second neural stimulation pulses to one or more of the electrode configurations with a lowest first capture threshold for motor fiber activity. Information is received by the external device related to one or more physiological responses that are induced in response to delivery of the second neural stimulation pulses to each of the plurality of electrode configurations.

In Example 19, the method according to Example 18, wherein the one or more physiological responses include intended physiological activity and intolerable physiological activity, and wherein the method further comprises generating an output on the external device that prioritizes the one or more electrode configurations that induce intended physiological activity based on a second capture threshold for the intended physiological activity.

In Example 20, the method according to Example 19, and further comprising programming the IMD with the external device to deliver therapy to at least one of the one or more electrode configurations that induce intended physiological activity at a lowest second capture threshold.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
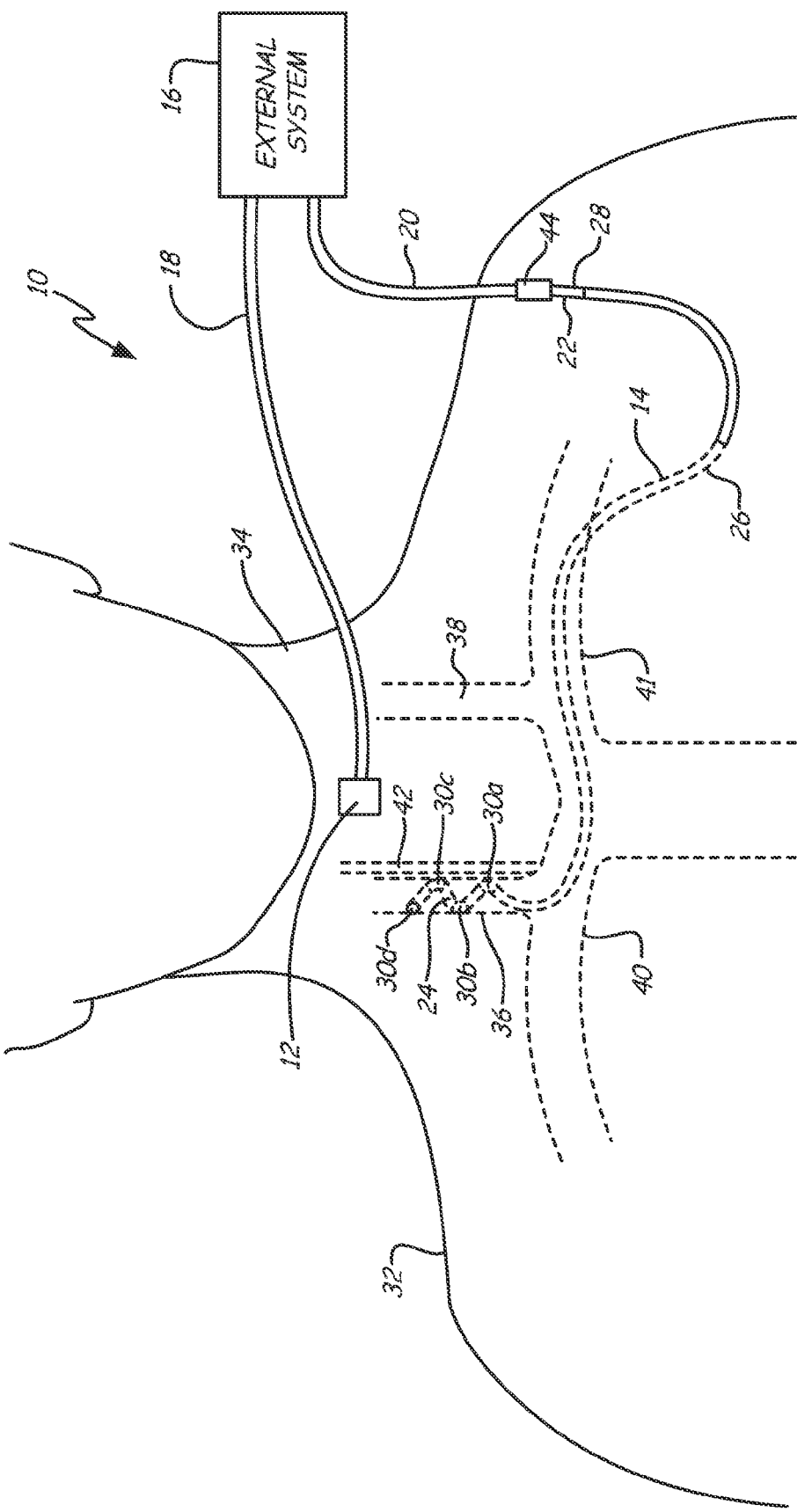
FIG. 1 shows an embodiment of a neurostimulation system and portions of an environment in which the neurostimulation system is used.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is an illustration of an embodiment of a neural stimulation system 10 and portions of an environment in which the system 10 is used. The system 10 includes an activity sensor 12 for sensing physiological activity, a transvenous lead 14 for delivering vagal nerve stimulation, and an external system 16 coupled to the activity sensor 12 via a cable 18 and coupled to the lead 14 via a cable 20. The external system 16, which in some embodiments is a programmer, allows for optimization of the vagal nerve stimulation using the sensed physiological activity. Examples of physiological activity that activity sensor 12 may be configured to sense include motor fiber activity, such as laryngeal activity and muscle activity, cough, change in blood pressure, change in heart rate, and/or evoked nerve response.

The lead 14 is a transvenous lead having a proximal end 22, a distal end 24, and an elongate body 26 coupled between the proximal end 22 and distal end 24. The proximal end 22 includes a connector 28. In the illustrated embodiment, the distal end 24 includes stimulation electrodes 30*a*, 30*b*, 30*c*, and 30*d*. As illustrated in FIG. 1, a body 32 includes a neck 34, a right internal jugular vein 36, a left internal jugular vein 38, a right subclavian vein 40, and a left subclavian vein 41. The lead 14 is inserted using techniques similar to those employed in implanting cardiac pacing leads. During the insertion, the distal end 24 enters the left subclavian vein 41 through an incision, advances in the left subclavian vein 41 and then the right subclavian vein 40 toward the right internal jugular vein 36, enters the right internal jugular vein 36, advances in the right internal jugular vein 36 until the electrodes 30*a*-30*d* reach one or more vagal nerve stimulation sites. After the distal end 24 is in the right internal jugular vein 36, the stimulation electrodes 30*a*-30*d* are positioned, and repositioned when necessary, using the lead 14 and/or a lead insertion tool such as a stylet, a guide wire, or a guide catheter.

The electrodes 30*a*-30*d* allow neural stimulation to be delivered to a vagus nerve 42, which is adjacent to the right internal jugular vein 36 in the cervical region. In some embodiments, the activity sensor 12 is placed on the neck over the larynx to sense a signal indicative of laryngeal activity. In some embodiments, the activity sensor 12 is substantially similar to the laryngeal activity sensor described in U.S. Patent App. Pub. No. 2008/0058874, which is hereby incorporated by reference in its entirety. The laryngeal activity is used as a measure of response of the vagus nerve 42 to the neural stimulation delivered to the vagus nerve 42. In various embodiments, the laryngeal activity is monitored for placement of stimulation electrodes such as the electrodes 30*a*-30*d*, optimization of stimulation parameter such as those controlling stimulation intensity (e.g., stimulation amplitude, frequency, duration, and duty cycle), and detection or monitoring of various events that affect the response of the vagal nerve 42 to the neural stimulation.

While the electrodes 30*a*-30*d* are arranged to provide stimulation to the vagus nerve 42, the lead 14 and electrodes 30*a*-30*d* may be positioned to provide stimulation to other portions of the autonomic nervous system. For example, the lead 14 may alternatively be positioned to provide stimulation to baroreceptors or the spinal cord.

As illustrated in FIG. 1, the proximal end 22 remains outside of the body 32, such as during an operation of implantation of the lead 14 and an implantable medical device such as one discussed below with reference to FIG. 2. This allows the electrodes 30*a*-30*d* to be placed as desired before connecting the proximal end 22 to the implantable medical device. The proximal end 22 includes a connector 28 coupled to a connector 44 of the cable 20 to allow delivery of the neural stimulation from the external system 16. The external system 16 allows a user such as a physician or other caregiver to control the delivery of neural stimulation via the lead 14 and monitor the signal indicative of larynx sensed by the activity sensor 12.

The configuration of the system 10 shown in FIG. 1 is an example presented for illustrative purposes. The present subject matter generally includes monitoring and optimization of nerve stimulation delivered using any electrode configuration using any signal that indicates physiological activity resulting from the vagal nerve stimulation. For example, the lead 14 may include one or more stimulation electrodes, and an electrode pair for delivering the neural stimulation may include two electrodes on the lead 14 or an electrode on the lead 14 and a reference electrode not necessarily adjacent to the vagus nerve. In addition, while four electrodes 30*a*-30*d* are shown, the lead may include more or fewer electrodes 30 on the lead 14. In some embodiments, the reference electrode is a skin patch electrode for acute use. In some embodiments, in addition to, or instead of, the stimulation electrodes 30*a*-30*d* on the lead 14, one or more nerve cuff electrodes each surrounding vagus nerve 42 are used. Other possible electrode configurations include a wrap electrode and/or spiral, straight, or biased multipolar electrode configurations. In some embodiments, the electrodes 30*a*-30*d* are placed in the left interval jugular vein 38. In these embodiments, during the insertion, the distal end 24 enters the left subclavian vein 41 or right subclavian vein 40 through an incision, enters the left internal jugular vein 38 from right subclavian vein 40, advances in the left internal jugular vein 38 until the electrodes 30*a*-30*d* reach one or more vagal nerve stimulation sites. Other implantation methods are also possible, such as implanting the lead in the carotid sheath in the cervical region or other extravascular locations near the neural target.

Further, while a single lead 14 is shown in FIG. 1, the system 10 can be configured to included a plurality of leads disposed in different locations in the patient. For example, the plurality of leads can be positioned such that each lead is adapted to provide different types of physiological responses. In such a configuration, the automatic electrode configuration described herein may be performed on each of the leads individually to optimize the neural response. In some exemplary implementations, the system 10 is configured to provide bilateral vagus nerve stimulation, multi-lead stimulation of the left and/or right vagus nerve, multi-lead spinal cord stimulation, stimulation of baroreceptors, or combinations thereof.

Figure 2:
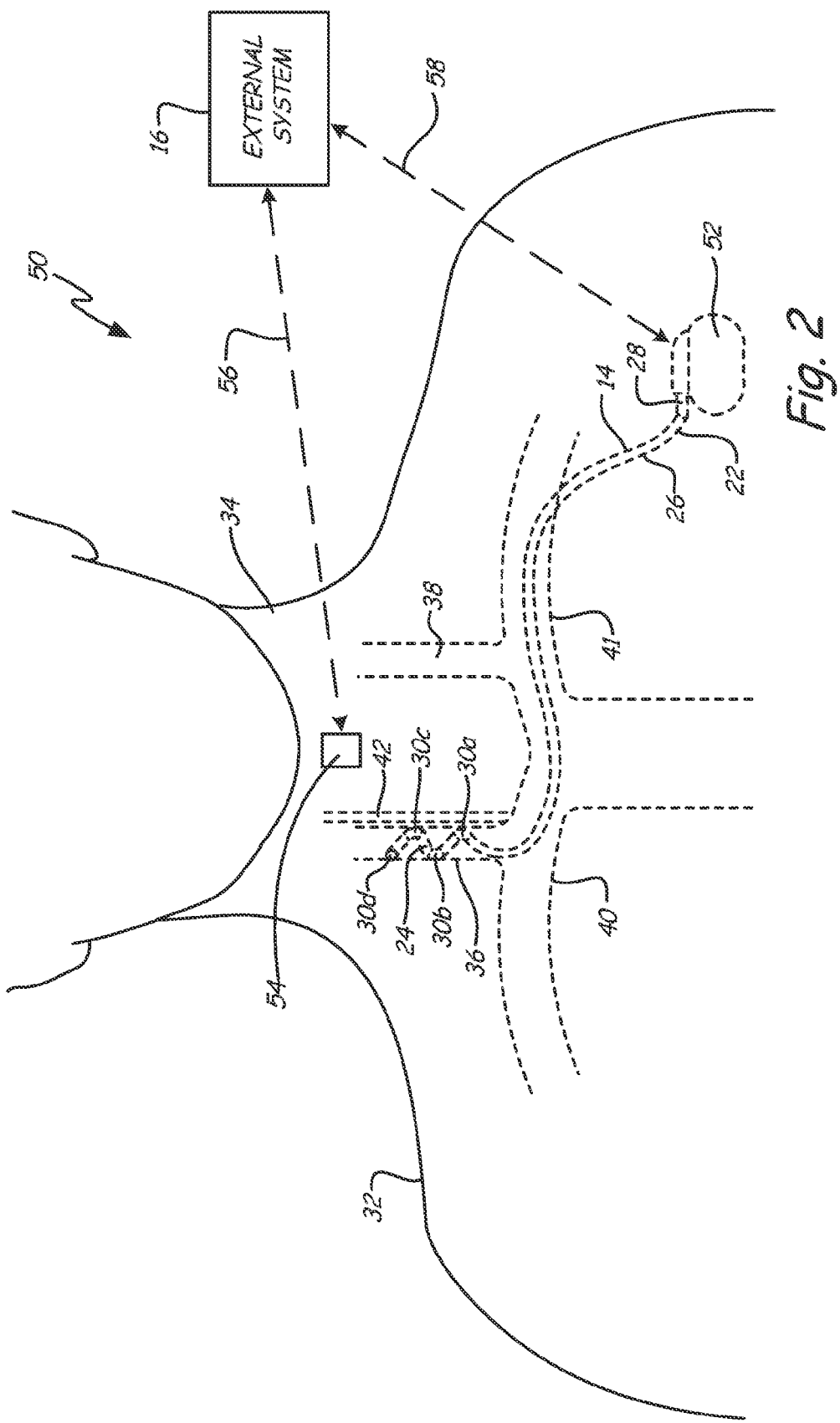
FIG. 2 shows another embodiment of a neurostimulation system and portions of an environment in which the neurostimulation system is used.

FIG. 2 is an illustration of an embodiment of a neural stimulation system 50 and portions of the environment in which the system 50 is used. The system 50 differs from the system 10 primarily in that the neural stimulation is delivered from an implantable medical device 52 implanted in body 101. FIGS. 1 and 2 illustrate different stages of implantation and use of an implantable neural stimulation system. In particular, FIG. 1 illustrates a system setup in the middle of an implantation procedure during which the lead 14 is inserted with the electrodes 30*a*-30*d* placed to achieve desirable performance of vagal nerve stimulation. FIG. 2 illustrates the system set-up after the implantable neural stimulation system is fully implanted, such as during the end stage of the implantation procedure when the implantable neural stimulation system is programmed for chronic use or during a follow-up examination during which the implantable neural stimulation system is adjusted if necessary.

An activity sensor 54 represents an embodiment of the activity sensor 12 (FIG. 1) that is capable of communicating with the external system 16 via a wireless link. In some embodiments, the activity sensor 54 and external system 16 are wirelessly coupled through telemetry, represented as a communication link 56, such as a radio-frequency electromagnetic telemetry link.

The implantable medical device 52 delivers the neural stimulation through any combination of the electrodes 30*a*-30*d*. After the electrodes 30*a*-30*d* are placed, the proximal end 22 of the lead 14 is connected to the implantable medical device 52 via the connector 28. During operation, the lead 14 delivers electrical signals between the IMD 52 and the electrodes 30a-30d. The electrodes 30a-30d may be separately controlled by the IMD 52, such that energy having different magnitude, phase, and/or timing characteristics may be delivered to or from each of the electrodes 30a-30d. In some embodiments, the housing of the implantable medical device 52 functions as a reference electrode, and the neural stimulation can be delivered using any electrodes selected from the electrodes 30a-30d and the housing of the implantable medical device 52. In some embodiments, neural activity in the vagus nerve 42 is sensed using any single or combined electrodes selected from the electrodes 30a-30d and the housing of the implantable medical device 52. In some embodiments, in addition to the neural stimulation circuit, the implantable medical device 52 includes other monitoring or therapeutic circuits or devices such as one or more of cardiac pacemaker, cardioverter/defibrillator, drug delivery device, and biological therapy device. The system 50 may alternatively be configured to include a plurality of leads 14, as discussed above.

Stimulating the sympathetic and parasympathetic nervous systems can have effects on physiological parameters associated with the heart, such as heart rate and blood pressure. In addition, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

The vagus nerve 42 has afferent properties, such that the neural stimulation is transmitted to the central nervous system (CNS). Vagal stimulation simultaneously increases parasympathetic and decreases sympathetic activity, and is believed to prevent further remodeling or predisposition to fatal arrhythmias in post-MI patients, to help restore autonomic balance and increase heart rate variability (HRV), to increase parasympathetic and reduce sympathetic tone in hypertrophic cardiac myopathy (HCM), neurogenic hypertension, and arrhythmia protection, to reduce anginal symptoms, to increase coronary blood flow (CBF), and to prevent development or worsening of congestive heart failure (CHF) following MI. The electrodes 30a-30d may be configured and arranged to stimulate the vagus nerve 42 to provide any of the physiological responses described. While the electrodes 30a-30d are shown arranged proximate the right vagus nerve 42 in FIGS. 1 and 2, the electrodes 30a-30d can be configured and arranged to stimulate the left vagus nerve to treat other physiological and psychological conditions, such as epilepsy and depression.

The external system 16 provides for control of and communication with the implantable medical device 52 by the user. The external system 16 and the implantable medical device 52 are communicatively coupled via a telemetry link 58. In some embodiments, the external system 16 includes a programmer. The external system 16 can be used to adjust the programmed therapy provided by the IMD 52, and the IMD 52 can report device data (e.g. battery information and lead resistance) and therapy data (e.g., sense and stimulation data) to the programmer using radio telemetry, for example.

In other embodiments, the external system 16 is a patient management system including an external device communicating with the implantable medical device 52 via the telemetry link 58, a remote device in a remote location, and a telecommunication network linking the external device and the remote device. The patient management system allows access to the implantable medical device 52 from the remote location, for purposes such as monitoring patient status and adjusting therapies. In some embodiments, the telemetry link 58 is an inductive telemetry link. In alternative embodiments, the telemetry link 58 is a far-field radio-frequency telemetry link.

Figure 3:
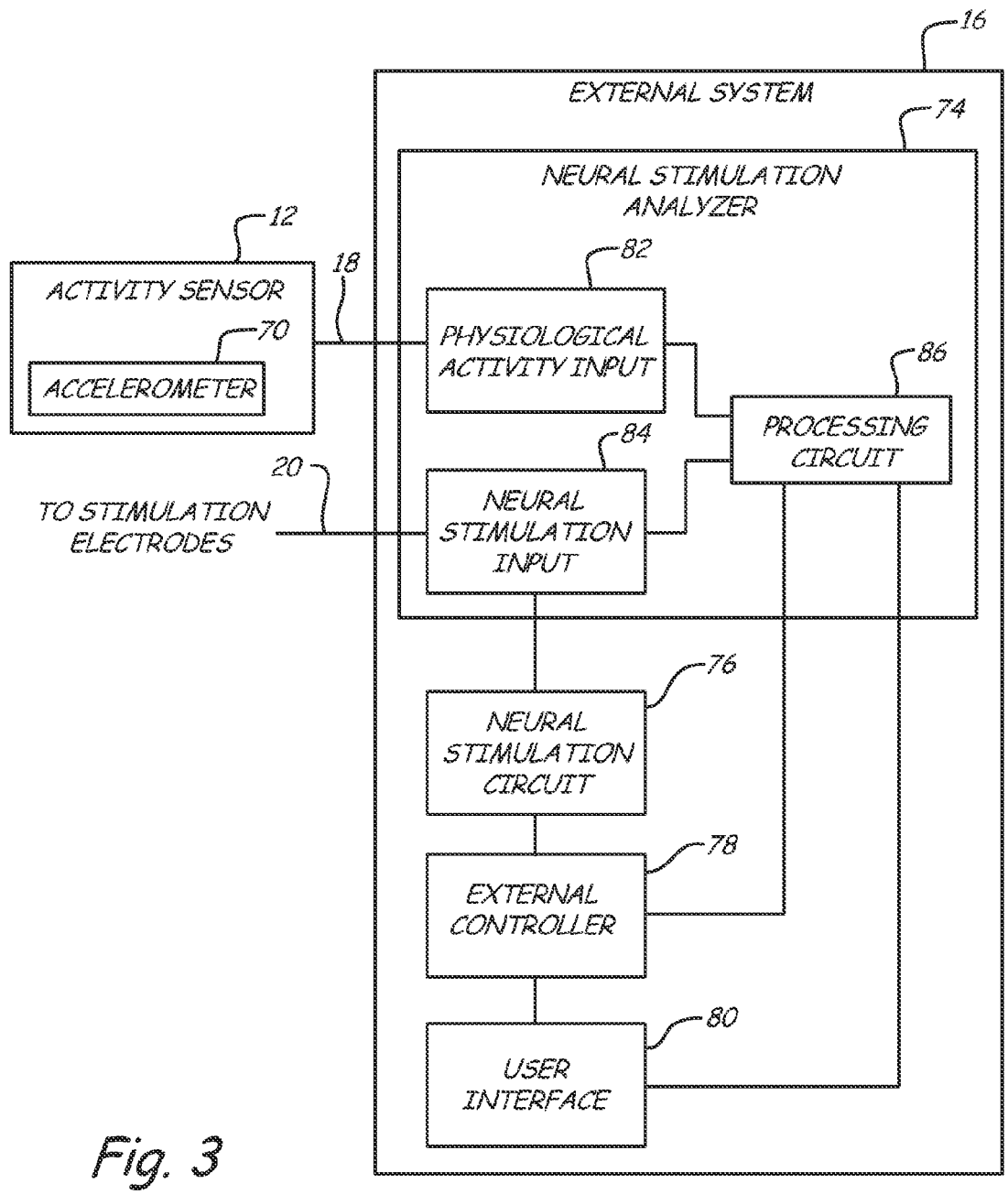
FIG. 3 is a block diagram illustrating an embodiment of portions of the neurostimulation system shown in FIG. 1.

FIG. 3 is a block diagram illustrating an embodiment of portions the system 10 (FIG. 1), including the activity sensor 12 and the external system 16. In some embodiments, the activity sensor 12 includes an accelerometer 70 to sense an acceleration signal being the signal indicative of physiological activity. The accelerometer 70 has characteristics suitable for sensing the magnitude and frequency of vibrations of the larynx that indicate activity in the vagus nerve when vagal nerve stimulation is delivered. In some embodiments, the accelerometer 70 represents a plurality of accelerometers allowing for selection of an acceleration signal as the signal indicative of physiological activity based on the signal quality.

The external system 16 includes a neural stimulation analyzer 74, a neural stimulation circuit 76, an external controller 78, and a user interface 80. The neural stimulation circuit 76 delivers the neural stimulation to stimulation electrodes such as electrodes 30a-30d. The external controller 78 controls overall operation of the external system 16, including the delivery of the neural stimulation from the neural stimulation circuit 76. In some embodiments, the external controller 78 controls the neural stimulation circuit 76 to deliver neural stimulation to a plurality of electrode configurations, each electrode configuration including one or more of the electrodes 30a-30d. The user interface 80 allows the user to control the neural stimulation and monitor the response of the vagus nerve to the neural stimulation. In some embodiments, the user interface 80 includes a display that provides a visual output relating to the response of the vagus nerve to the neural stimulation.

The neural stimulation analyzer 74 includes a physiological activity input 82, a neural stimulation input 84, and a processing circuit 86. The physiological activity input 82 receives a signal indicative of physiological activity from the activity sensor 12 via the cable 18. In an alternative embodiment, the system 10 does not include an activity sensor 12, and clinician observations relating to physiological activity are provided to the physiological activity input 82 manually by a clinician. The neural stimulation input 84 receives a signal indicative of the delivery of the neural stimulation to the vagus nerve. The processing circuit 86 processes the signal indicative of physiological activity for analyzing the operation and performance of system 10 using that signal. In addition, the processing circuit 86 associates the electrode configurations that induce physiological activity with a threshold energy level at which the physiological activity is induced.

Figure 4:
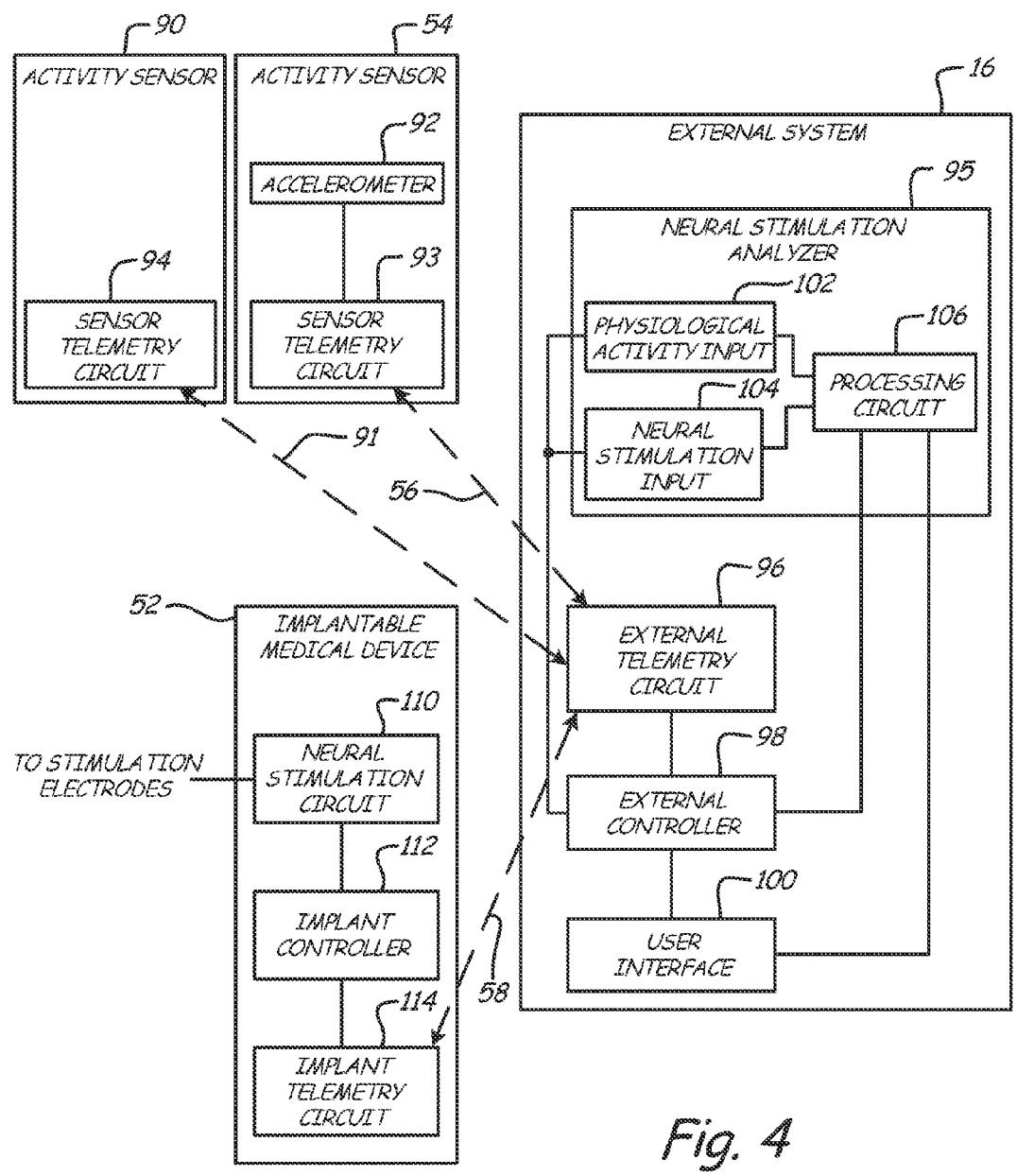
FIG. 4 is a block diagram illustrating an embodiment of portions of the neurostimulation system shown in FIG. 2.

FIG. 4 is a block diagram illustrating an embodiment of portion of the system 50, including the activity sensor 54 coupled to the external system 16 via the communication link 56, the implantable medical device 52 coupled to the external system 16 via the communication link 58. In some embodiments, the system 50 includes one or more additional physiological activity sensors 90 coupled to the external system 16 via a communication link 91. The activity sensor 54 includes an accelerometer 92 and a sensor telemetry circuit 93. In the illustrated embodiment, the communication link 56 is a telemetry link. The sensor telemetry circuit 93 transmits the sensed signal indicative of physiological activity (e.g., motor fiber activity) to the external system 16 via the telemetry link 56.

The one or more physiological activity sensors 90 include sensor telemetry circuitry 94 that transmits signals indicative of physiological activity to the external system 16 via the telemetry link 56. According to some embodiments, the physiological activity sensors 90 include sensor assemblies to sense automatic nervous system (ANS) activity. The sensor can be used to provide feedback in a closed-loop. Examples of physiological activity capable of being detected by the one or more physiological activity sensors 90 include coughing, voice-related physiological activity, such as voice alterations or laryngismus, respiratory-related physiological activity, such as dyspnea and apnea, cardiac-related physiological activity, such as heart rate modulation, bradycardia, tachyarrhythmias, and reduced cardiac output, and patient discomfort, such as nausea, inflammation of throat, abnormal sensations, and upset stomach. The one or more physiological activity sensors 90 can include various types of sensors and circuitry to detect physiological activity. For example, an impedance sensor, an accelerometer and/or acoustic sensor can be used to detect coughing. An acoustic sensor can also be used to detect voice-related physiological activity. Respiratory sensors, such as minute ventilation and transthoracic impedance, can be used to detect respiratory-related physiological activity. Cardiac-related physiological activity can be detected using heart rate sensors, arrhythmia detectors, blood pressure sensors, and blood flow sensors. Patient and/or physician inputs related to patient discomfort may also be provided to the external device 16. Example embodiments of sensors suitable for the physiological activity sensors 90 are described in, for example, U.S. Pat. No. 7,561,923, U.S. Patent App. Pub. No. 2008/0086181, and U.S. Patent App. Pub. No. 2008/0051839, each of which is incorporated by reference in its entirety.

The external system 16 includes a neural stimulation analyzer 95, an external telemetry circuit 96, an external controller 98, and a user interface 100. The external telemetry circuit 96 receives the signal indicative of physiological activity from the activity sensor 54 via the communication link 56 and, in some embodiments, signals indicative of physiological activity from the one or more physiological activity sensors 90 via the communication link 91. The external telemetry circuit 96 also communicates with the implantable medical device 52 via the telemetry link 58 to control the neural stimulation delivered from by the implantable medical device 52. The external controller 98 controls overall operation of the external system 16, including the transmission of commands for controlling the neural stimulation delivered from the implantable medical device 52.

In this embodiment, the neural stimulation analyzer 95 includes a physiological activity input 102, a neural stimulation input 104, and a processing circuit 106. The physiological activity input 102 receives inputs indicative of physiological activity from the activity sensor 12 via the communication link 56. In some embodiments, the physiological activity input 102 also receives inputs from the one or more physiological activity sensors 90 indicative of physiological activity generated during neural stimulation. In an alternative embodiment, the system 50 does not include an activity sensors 52 and/or 90, and clinician observations relating to physiological activity are provided to the physiological activity input 102 manually by a clinician. The neural stimulation input 104 receives a signal indicative of the delivery of the neural stimulation to the vagus nerve. The processing circuit 106 processes the signals indicative of physiological activity for analyzing the operation and performance of system 50. In addition, the processing circuit 106 associates the electrode configurations that induce physiological activity with threshold energy levels at which the physiological activity are induced.

The implantable medical device 52 includes a neural stimulation circuit 110, an implant controller 112, and an implant telemetry circuit 114. The neural stimulation circuit 110 delivers the neural stimulation through stimulation electrodes such as electrodes 30a-30d. The implant controller 112 controls the delivery of the neural stimulation and is responsive to the commands transmitted from the external system 16. The implant telemetry circuit 114 receives the commands from the external system 16 via the telemetry link 58 and when needed, transmits signals to the external system 16 via the telemetry link 58.

The systems shown in FIGS. 1-4 are configured to facilitate selection of one or more electrode configurations induce intended physiological activity at low energies when neural stimulation signals are applied. The one or more electrode configurations include combinations of one or more of the electrodes 30a-30d to which the neural stimulation signals are applied. The external system 16 is employed to receive information related to physiological activity that occurs in response to the neural stimulation signals applied to each electrode configuration and provide an output that assists a clinician in determining an optimal or preferred electrode configuration(s). The selected one or more electrode configurations may be a function of the capture threshold of the physiological activity. As discussed above, FIGS. 1 and 3 illustrate system configurations for selecting suitable electrode configurations during implantation of the lead 14 to get optimal positioning, and FIGS. 2 and 4 illustrate system configurations for selecting suitable electrode configurations after the IMD 52 has been implanted for a period of time (e.g., at a follow-up visit after implantation).

Figure 5:
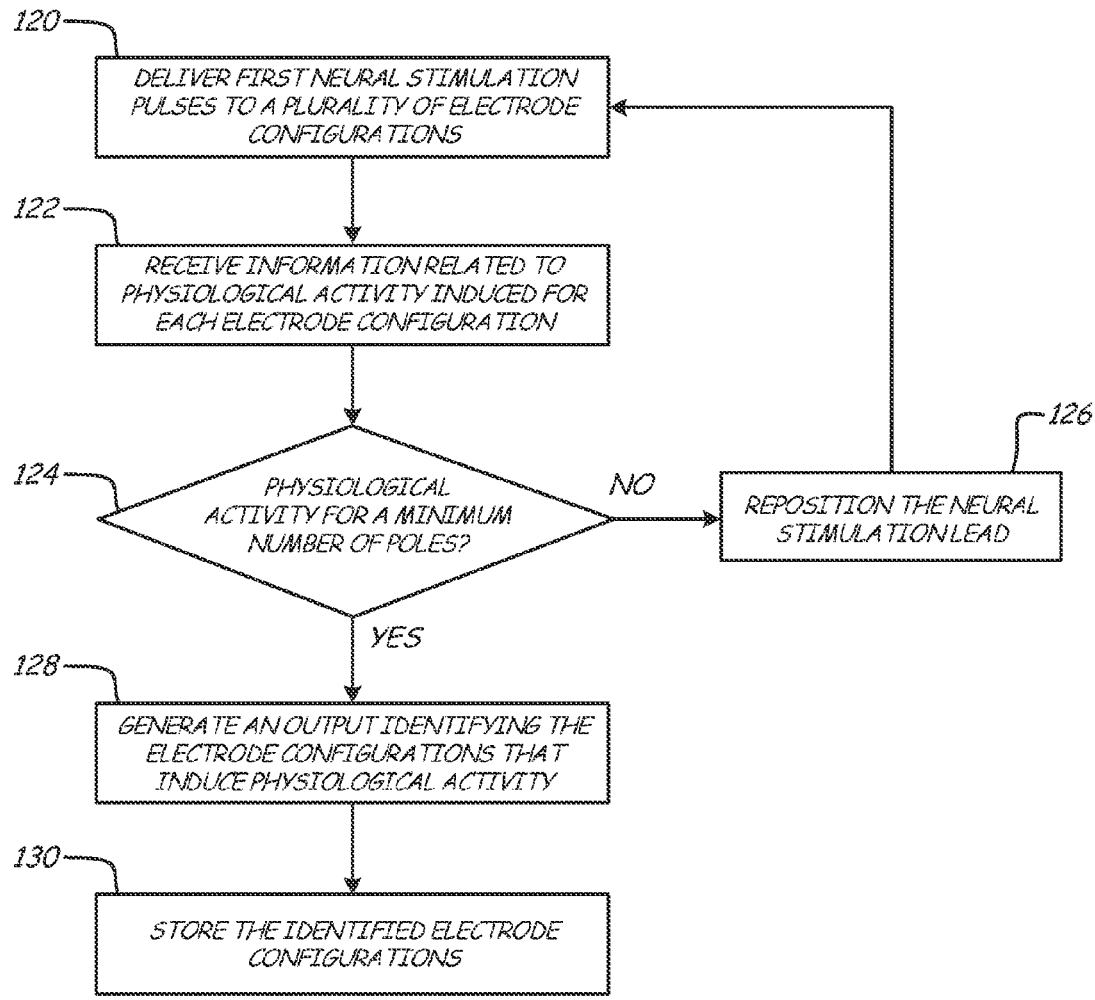
FIG. 5 is a flow diagram illustrating an embodiment of a process for selecting electrode configurations during implantation and positioning of a neural stimulation lead in the neurostimulation system shown in FIGS. 1 and 3.

FIG. 5 is a flow diagram illustrating an embodiment of a process for selecting electrode configurations during implantation and positioning of the lead 14 in the neurostimulation system shown in FIGS. 1 and 3. Initially, the clinician positions the lead 14 and electrodes 30a-30d proximate the nerve 42. In some embodiments, the lead 14 is connected to the external device 16 via a cable 20, as shown in FIG. 1. In an alternative embodiment, the lead 14 is connected to the IMD 52 and controlled via a cable or telemetrically prior to implantation of the IMD 52.

In step 120, the external device 16 controls the neural stimulation circuit 76 to deliver first neural stimulation pulses to a plurality of configurations of the electrodes 30a-30d. The amplitude of the first stimulation pulses is selected to induce physiological activity in the patient. In some embodiments, the external device 16 systematically cycles through delivery of stimulation pulses to multiple electrode configurations. In some embodiments, the electrode configurations are bipolar configurations. In other embodiments, the electrode configurations are unipolar configurations or include more than two electrodes. The electrode configurations may include some or all of the possible combinations of the electrodes 30a-30d for the number of poles selected. That is, a clinician may be able to omit certain electrode configurations as being known to not generate a response (e.g., the electrodes are too far apart to provide a response). For example, if the lead 14 includes four electrodes 30-30d as shown in FIG. 1, and bipolar stimulation is being tested, the external device 16 delivers stimulation pulses to up to six electrode configurations: 30a and 30b, 30a and 30c, 30a and 30d, 30b and 30c, 30b and 30d, and 30c and 30d. As another example, if the lead 14 includes eight electrodes, and bipolar stimulation is being tested, the external device delivers stimulation pulses to up to 28 electrode configurations.

In some embodiments, the external device 16 controls the neural stimulation circuit 76 to deliver the first neural stimulation pulses at more than one energy level for each of the electrode configurations. In one exemplary implementation, the external device 16 controls the neural stimulation circuit 76 to deliver the first stimulation pulses at 1 mA and 2 mA. The delivery of the first stimulation pulses at a plurality of energy levels helps identify the capture threshold for various electrode configurations.

In step 122, the external device 16 receives information related to physiological activity induced for each electrode configuration. The physiological activity may include, for example, motor fiber activity, such as laryngeal vibrations. In some embodiments, the information related to physiological activity is received in the form of signals from the activity sensor 12 provided to the physiological activity input 82. In other embodiments, the information related to physiological activity is provided as an input to the external system 16 on the user interface 80 based on, for example, observations by the clinician.

In decision step 124, the external device 16 determines whether physiological activity is provided for a minimum number of poles (i.e., electrode configurations). For example, the external device 16 may display the results of step 122, and the clinician may decide whether the number of electrode configurations that induced physiological activity is satisfactory. Alternatively, the minimum number of poles that provide a laryngeal response may be programmed into the external device 16, and the external device 16 may display a message or alert that the minimum number of poles did not provide physiological activity.

If, in decision step 124, a minimum number of poles does not produce physiological activity, then, in step 126, the clinician repositions the lead 14 such that the electrodes 30a-30d are positioned differently relative to the nerve 42. In some embodiments, the electrodes 30a-30d are moved cranially. In other embodiments, the electrodes 30a-30d are moved caudally. The process then returns to step 120 to again test a plurality of electrode configurations.

If, in decision step 124, the minimum number of poles does produce physiological activity, then, in step 128, the external device 16 generates an output that identifies the electrode configurations that induce physiological activity. For example, in some embodiments, the external device 16 displays the electrode configurations that induce physiological activity. In embodiments in which the activity sensor 12 detects the physiological activity, the external device 16 may also display the magnitude of physiological activity. In embodiments in which the external device 16 controls the neural stimulation circuit 76 to deliver the first neural stimulation pulses at more than one amplitude, the external device 16 may display the amplitude at which each electrode configuration induces physiological activity (i.e., capture threshold).

In step 130, the external device 16 may facilitate storage of the electrode configurations identified in step 128. For example, the external device 16 may store the electrode configurations, as well as any associated physiological activity magnitudes and capture thresholds, locally in a memory in the external device 16 or may transmit the information to a central server. The external device 16 may additionally or alternatively provide the information related to the identified electrode configurations for storage in the patient's record for future reference. Steps 120-130 may be repeated for upright and supine postures.

When the number of electrode configurations that induce physiological activity is satisfactory, the lead 14 may be connected to the IMD 52, and the implantation procedure may be completed. After implantation, natural shifting of the lead 14 relative to the nerve 42 and tissue formation around the lead 14 and electrodes 30a-30d may have an effect on the electrode configurations that induce physiological activity. That is, the capture thresholds of the identified electrode configurations may change, or the electrode configurations that induce physiological activity may change.

Figure 6:
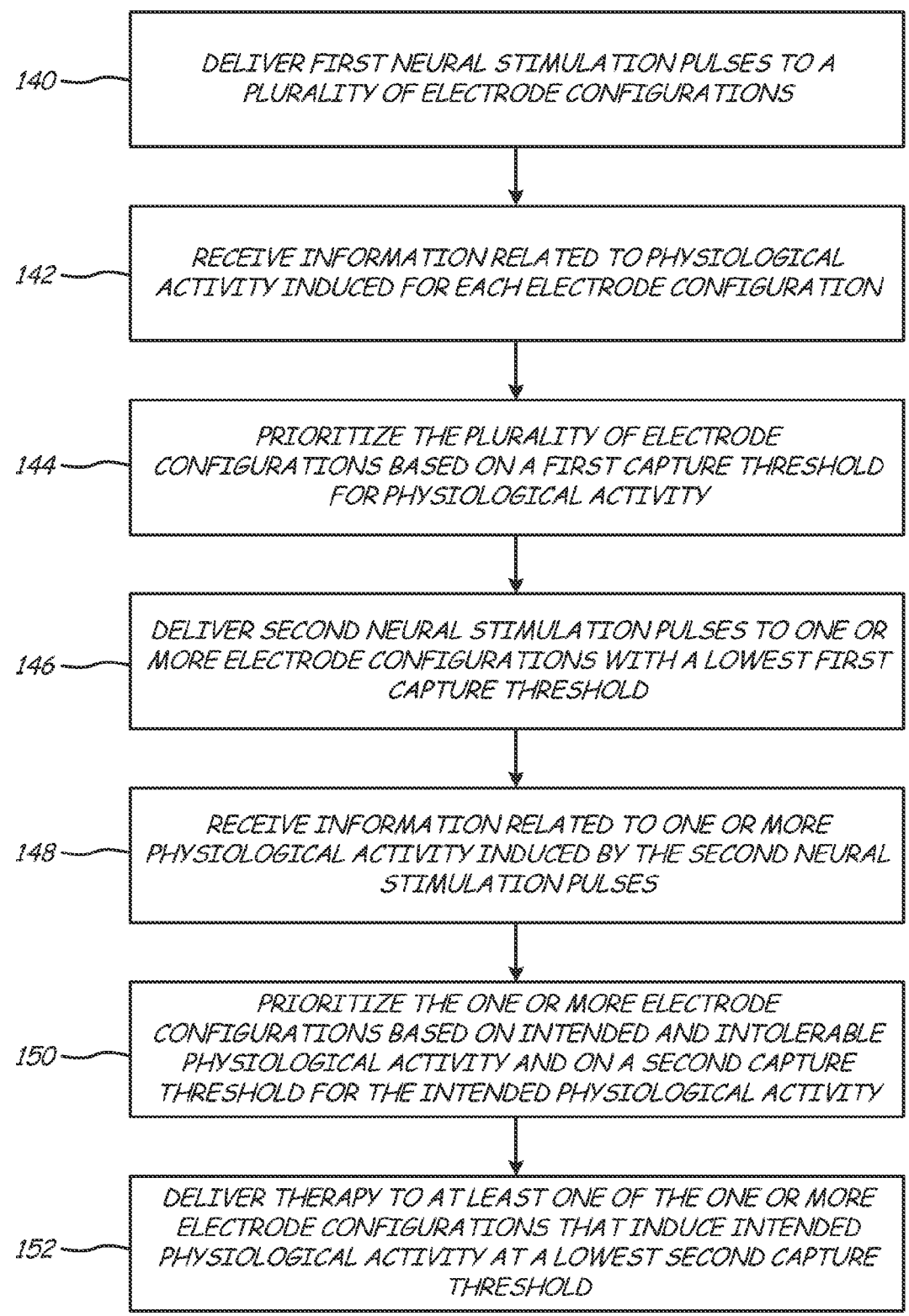
FIG. 6 is a flow diagram illustrating an embodiment of a process for selecting electrode configurations after implantation of an implantable medical device in the neurostimulation system shown in FIGS. 2 and 4.

FIG. 6 is a flow diagram illustrating an embodiment of a process for selecting electrode configurations after implantation of an implantable medical device in the neurostimulation system shown in FIGS. 2 and 4. In step 140, the external device 16 controls the neural stimulation circuit 110 in the IMD 52 to deliver first neural stimulation pulses to a plurality of configurations of the electrodes 30a-30d, similar to the process described above with respect to FIG. 5. In some embodiments, the external device 16 controls the neural stimulation circuit 110 to deliver the first neural stimulation pulses at more than one energy level for each of the electrode configurations.

In step 142, the external device 16 receives information related to physiological activity induced for each electrode configuration. The physiological activity may include, for example, motor fiber activity, such as laryngeal vibrations. In some embodiments, the information related to physiological activity is received in the form of signals from the activity sensor 54 provided to the physiological activity input 102. In this embodiment, the physiological activity input 102 is configured to receive signals related to physiological activity induced by neural stimulation signals. In other embodiments, the information related to physiological activity is provided as an input to the external system 16 on the user interface 100 based on, for example, observations by the clinician.

In some embodiments, the external device 16 may then compare the electrode configurations that induce physiological activity post-implantation with the electrode configurations that induce physiological activity pre-implantation. In addition, the external device 16 may compare the pre- and post-implantation capture thresholds for each of the electrode configurations. This information can help the clinician determine, for example, whether the lead 14 has shifted since implantation and whether electrode configurations different than those identified during implantation would be more suitable for long term therapy delivery.

In step 144, the external device 16 prioritizes the plurality of electrode configurations based on the capture threshold for each of the electrode configurations. For example, the external device 16 may display the electrode configurations in groups based on the lowest capture threshold at which physiological activity is induced. For example, the external device 16 may display the electrode configurations that induce physiological activity at 1 mA in one group and the electrode configurations that induce physiological activity at 2 mA in another group.

In step 146, the external device 16 controls the neural stimulation circuit 110 to deliver second neural stimulation pulses to one or more electrode configurations with a lowest capture threshold for physiological activity. In an alternative embodiment, the external device 16 controls the neural stimulation circuit 110 to deliver second neural stimulation pulses to all electrode configurations that induced physiological activity. In some embodiments, the neural stimulation circuit 110 is controlled to deliver the second neural stimulation pulses at more than one amplitude. The second neural stimulation pulses, which in some embodiments has an amplitude greater than the first neural stimulation pulses, are configured to induce additional physiological activity. For example, the second neural stimulation pulses may induce intended physiological activity such as heart rate modulation, atrioventricular (AV) conduction, and/or changes to the QRS complex and T wave electrocardiogram characteristics. The second neural stimulation pulses may also induce intolerable or undesirable physiological activity, such as those discussed above.

In step 148, the external device 16 receives information related to the physiological activity induced by the second neural stimulation signals for each electrode configuration tested. In some embodiments, the information related to the induced physiological activity is received in the form of signals from the one or more physiological activity sensors 90 provided to the physiological activity input 102. In other embodiments, the information related to induced physiological activity is provided as an input to the external system 16 on the user interface 100 based on, for example, observations by the clinician or statements by the patient.

In step 150, the external device 16 prioritizes the plurality of electrode configurations based on which electrode configurations induce intended and intolerable physiological activity, and based on the capture threshold at which intended physiological activity occur for each of the electrode configurations. For example, the external device 16 may display the one or more electrode configurations that induce physiological activity in groups based on the lowest capture threshold at which one or more intended physiological responses are induced. The external device 16 may also exclude any of the electrode configurations that induce intolerable physiological activity. The external device 16 may then display one or more recommended electrode configurations, along with a physiological activity profile for each of the electrode configurations. Steps 140-150 may be repeated for upright and supine postures.

In step 152, the clinician uses the external device 16 to program the IMD 52 to deliver therapy to at least one of the one or more electrode configurations that induce intended physiological activity at the lowest capture threshold. For example, if multiple electrode configurations provide similar intended physiological activity at the lowest capture threshold, the external device 16 programs the IMD to cycle through the electrode configurations periodically.

In some embodiments, the electrodes 30a-30d that are not employed for delivery of neural stimulation signals may be defaulted into a pool for use in other functions less impacted by the proximity of the electrode 30a-30d to the therapeutic neural fibers. For example, the electrodes 30a-30d that are not used for delivery of neural stimulation pulses may be employed to provide a wireless ECG vector to the IMD 52.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A neurostimulation system comprising:
an implantable neural stimulation device having a plurality of electrodes and a neural stimulation circuit, the plurality of electrodes configured for positioning proximate a portion of the autonomic nervous system, the neural stimulation circuit configured to deliver neural stimulation pulses through the plurality of electrodes;
a user interface, the user interfacing including a display; and
a controller configured to:
reduce a number of potential electrode combinations of the plurality of electrodes from a plurality of potential electrode combinations to a subset of potential electrode combinations for further testing, including:
control the neural stimulation circuit to deliver a first plurality of neural stimulation pulses to a neural target through the plurality of potential electrode combinations;
receive information indicative of physiological activity that is induced in response to the delivery of the first plurality of neural stimulation pulses;
use the information indicative of physiological activity to determine for each of the plurality of electrode combinations whether the first plurality of neural stimulation pulses captures neural tissue to induce physiological activity; and
group electrode combinations using the received information into the subset of potential electrode combinations that are associated with capturing neural tissue;
determine that the subset has at least a minimum number of potential electrode combinations for further testing, and identify on the display the subset of potential electrode combinations associated with capturing neural tissue; and
further test the subset of potential electrode combinations that has a least the minimum number of potential electrode combinations to further reduce the number of potential electrode combinations for delivering neurostimulation pulses to the neural target.

2. The neurostimulation system of claim 1, further comprising one or more physiological activity sensors configured to sense a signal indicative of the physiological activity and generate the information indicative of the physiological activity.

3. The neurostimulation system of claim 1, wherein the received information further comprises undesirable physiological activity induced in response to delivery of the first plurality of neural stimulation pulses.

4. The neurostimulation system of claim 3, wherein the controller is configured to remove from the subset any electrode combination associated with inducing the undesirable physiological activity.

5. The neurostimulation system of claim 1, wherein the physiological activity is associated with motor fiber activity.

6. The neurostimulation system of claim 1, wherein the controller is configured to:
control the neural stimulation circuit to deliver a second plurality of neural stimulation pulses to the neural target to further test the subset of potential electrode combinations, and receive additional information related to physiological activity that is induced in response to delivery of the second plurality of neural stimulation pulses.

7. The neurostimulation system of claim 6, wherein the second plurality of neural stimulation pulses are delivered at a higher pulse amplitude than the first plurality of neural stimulation pulses.

8. The neurostimulation system of claim 6, wherein the second plurality of neural stimulation pulses are delivered at a plurality of different amplitudes.

9. The neurostimulation system of claim 6, wherein the controller is configured to prioritize the electrode combinations of the subset based on the additional information.

10. The neurostimulation system of claim 6, wherein the controller is configured to control the neural stimulation circuit to deliver the first plurality of neural stimulation before the implantable neural stimulation device is fully implanted and to deliver the second plurality of neural stimulation after the implantable neural stimulation device is fully implanted.

11. The neurostimulation system of claim 1, wherein the controller is configured to prioritize the electrode combinations of the subset that induce intended physiological activity based on a second capture threshold and indicate the second subset on the display.

12. The neurostimulation system of claim 11, wherein the controller is configured to control the neural stimulation circuit to deliver therapy through at least one electrode combination of the subset.

13. The neurostimulation system of claim 1, wherein the controller is an external controller and is configured to communicate with the implantable neural stimulation device.

14. The neurostimulation system of claim 1, wherein the controller is part of the implantable neural stimulation device.

15. A method of automatic assessment of a plurality of electrodes of an implantable neural stimulation device, the method comprising:
reducing a number of potential electrode combinations of the plurality of electrodes from a plurality of potential electrode combinations to a subset of potential electrode combinations for further testing, including;
delivering a first plurality of neural stimulation pulses to a neural target through the plurality of electrode combinations;
receiving information, at a controller, that is indicative of physiological activity that is induced in response to delivery of the first plurality of neural stimulation pulses;
using the information indicative of physiological activity to determine for each of the plurality of electrode combinations whether the first plurality of neural stimulation pulses captures neural tissue to induce physiological activity; and
grouping electrode combinations using the received information, including identifying, with the controller, the subset of potential electrode combinations associated with capturing neural tissue; and
determining that the subset has a at least a minimum number of potential electrode combinations for further testing, and displaying, on a display, identification of the subset of more than one of the plurality of electrode combinations associated with capturing neural tissue; and
further testing the subset of potential electrode combinations that has at least the minimum number of potential electrode combinations to further reduce the number of potential electrode combinations for delivering neurostimulation pulses to the neural target.

16. The method of claim 15, wherein the received information further comprises undesirable physiological activity induced in response to the delivery of the first plurality of neural stimulation pulses, and wherein identifying the subset further comprises removing from the subset any electrode combination associated with inducing the undesirable physiological activity.

17. The method of claim 15, wherein further testing the subset of potential electrode combinations includes:
delivering a second plurality of neural stimulation pulses to the neural target through the subset of electrode combinations; and
receiving additional information, at the controller, related to physiological activity that is induced in response to delivery of the second plurality of neural stimulation pulses.

18. The method of claim 17, wherein the second plurality of neural stimulation pulses is delivered at a higher pulse amplitude than the first plurality of neural stimulation pulses.

19. The method of claim 17, wherein the second plurality of neural stimulation pulses is delivered at a plurality of different amplitudes.

20. The method of claim 17, further comprising:
prioritizing the electrode combinations of the subset based on the additional information; and
displaying, on the display, an indication of the prioritization of the electrode combinations.

* * * * *